United States Patent
van Straaten et al.

(10) Patent No.: US 9,057,669 B2
(45) Date of Patent: Jun. 16, 2015

(54) TRANSFER LINE FOR SAMPLING PROBE

(75) Inventors: Mark van Straaten, Heffen (BE); Wouter Van De Putte, Rotselaar (BE); Samuel Van Herreweghe, Pellenberg (BE)

(73) Assignee: MAVA AES NV, Steenokkerzeel (BE)

( * ) Notice: Subject to any disclaimer, the term of this patent is extended or adjusted under 35 U.S.C. 154(b) by 61 days.

(21) Appl. No.: 13/229,988

(22) Filed: Sep. 12, 2011

(65) Prior Publication Data

US 2012/0060630 A1    Mar. 15, 2012

Related U.S. Application Data

(60) Provisional application No. 61/382,182, filed on Sep. 13, 2010.

(30) Foreign Application Priority Data

Sep. 13, 2010  (EP) ..................... 10176429

(51) Int. Cl.
*G01N 33/24* (2006.01)
*G01N 1/22* (2006.01)
*E21B 49/00* (2006.01)

(52) U.S. Cl.
CPC .............. *G01N 1/2294* (2013.01); *E21B 49/00* (2013.01); *G01N 33/24* (2013.01)

(58) Field of Classification Search
CPC ... G01N 1/2294; G01N 33/24; G01N 33/241; G01N 33/246
USPC ........ 73/19.01, 19.1, 863.11, 863.12, 863.21, 73/863.23, 864, 864.34, 864.73, 864.74, 73/864.81
See application file for complete search history.

(56) References Cited

U.S. PATENT DOCUMENTS

| | | | | |
|---|---|---|---|---|
| 3,307,017 A | * | 2/1967 | Horstmann | 219/553 |
| 4,985,625 A | * | 1/1991 | Hurst | 250/288 |
| 5,010,776 A | * | 4/1991 | Lucero et al. | 73/863.23 |
| 5,180,475 A | * | 1/1993 | Young et al. | 204/454 |
| 5,358,057 A | * | 10/1994 | Peters et al. | 175/20 |
| 5,499,528 A | * | 3/1996 | Bahar | 73/23.2 |
| 5,587,538 A | * | 12/1996 | Bratton | 73/863.33 |
| 5,639,956 A | * | 6/1997 | Christy | 73/19.01 |
| 5,902,939 A | * | 5/1999 | Ballard et al. | 73/863.12 |
| 6,289,714 B1 | * | 9/2001 | Tartre | 73/19.01 |
| 6,487,920 B1 | * | 12/2002 | Robbat, Jr. | 73/863.12 |
| 6,978,688 B2 | * | 12/2005 | Engebretson | 73/863.23 |
| 7,520,186 B2 | * | 4/2009 | Risk | 73/864.74 |

OTHER PUBLICATIONS

Restek Silcosteel Brochure, 2005.*
Examination Report of EPO in EP10176429.8, Jul. 18, 2012.

* cited by examiner

*Primary Examiner* — Randy W Gibson
*Assistant Examiner* — Natalie Huls
(74) *Attorney, Agent, or Firm* — Bacon & Thomas, PLLC

(57) ABSTRACT

Methods of sampling substances such as subsurface contaminants, a transfer line for use in a system for such sampling, a sampling system and methods of manufacture and use of the system are described. The transfer line used in a probe system for subsurface chemical sampling connects a detection apparatus with a probe, the transfer line including a first flexible tube for carrying fluid to the probe; and a second flexible tube for carrying sample-loaded fluid from the probe; wherein second flexible or both first and second flexible tubes comprise a barrier tube surrounded by a metal coating. The metal coating is a continuous cladding deposited with structural integrity, and the metal coating is surrounded by an insulating layer, so that one or both of the flexible tubes can be heated by applying a voltage on the metal coating.

23 Claims, 4 Drawing Sheets

TRANSFER LINE FOR SAMPLING PROBE

FIELD OF THE INVENTION

This invention relates to sampling of substances such as subsurface contaminants, and to a transfer line for use in a system for the sampling of substances such as subsurface contaminants as well as to a sampling system and methods of manufacture and use of the system.

BACKGROUND TO THE INVENTION

Subsurface contaminants, such as volatile organic compounds (VOC) and semi-volatile organic compounds (SVOC), can be sampled by using an in situ penetrometer probe. One known type of penetrometer probe is a membrane interface probe developed by Geoprobe™. FIG. 1 shows a sampling system 10 of this kind. A probe 30 is advanced, or pushed, through soil by a hydraulic pushing device (not shown) and a set of pipes 29. The probe 30 includes a heating cartridge 34 for heating the soil 35 around the probe 30 and a semi-permeable membrane such as described in U.S. Pat. No. 5,639,956. The membrane prevents exit of carrier gas from the probe 30 to the soil. A transfer line 20 connects apparatus 40 on the surface with the probe 30. The transfer line 20 typically comprises a carrier gas tube 11 for carrying gas in the direction from the surface apparatus 40 to the probe 30, a collection gas tube 12 for carrying gas in the direction from the probe 30 to the surface apparatus 40, and electrical wiring. In use, a carrier gas is delivered from the surface apparatus 40 to an outlet 31 at the probe 30 via tube 11. Contaminants in the heated soil in the region 35 around the probe 30 are collected in the gas at the probe 30, e.g. through the semi-permeable membrane. Contaminant-loaded gas is then conveyed, via tube 12, to detector 42 at the surface. An alternative to the semi-permeable membrane is described in U.S. Pat. No. 6,487,920 with which system, the contaminants in the heated soil in the region 35 around the probe 30 are collected in the gas at the probe 30 directly through an opening and no semi-permeable membrane is used.

A flexible transfer line 20 is required as the line must pass through the pipe sections 29 when they are stacked. Therefore, the line should have a bending radius of approximately 30 cm or less. Also, as the internal diameter of the pipes 22 is approximately 20 mm, there is a restriction for the outer diameter of the transfer line 20.

One of the challenges in transporting the compounds to the surface is to minimise the loss of compounds in the transfer line. These losses in the transfer line can be caused by absorption and adsorption of the compounds at the inner surface of the tube 12 in transfer line 20. Secondly, due to the high moisture level of the collection gas, local moisture condensation in the tubes 11, 12 of the transfer line 20 can obstruct the gas flow, or can increase compound loss through condensation.

Even more important is the cross-contamination between samples which occurs when passing pure product zones (DNAPL's, Dense Non-Aqueous Phase layers, e.g. including tar and chorinated solvents). When passing DNAPL's, compounds are adsorbed on the inner wall of the transfer line. Therefore, the transfer line should be flushed with carrier gas in order to clean the transfer line. Flushing times are typically between 10-60 min which results in long waiting times for the drilling team. This of course is not economically efficient.

In order to minimise the problems relating to adsorption, absorption and condensation, heated transfer lines have been developed. Two methods of heating have been proposed. A first method of heating a transfer line is by wrapping a heating wire around the collection tube. This method suffers from weakness when bending which can result in cold spots and condensation problems. Since this bending capability is crucial when using these tubes for measurements in the field this is a very important prerequisite for the transfer line. A second method of heating a transfer line is shown in U.S. Pat. No. 6,487,920. This uses a silcosteel tube as a collection tube which is resistively heated. Both methods however are very inefficient as a heating method because they require high power, in the kilowatts region, to achieve the required temperatures. Moreover, since the methods are to be used also in remote field conditions where electrical power might not be readily available, additional heavy power generators are necessary. This hampers to a large extent the applicability of the prior art systems.

The methods used in the prior art suffer also from a lack of ease of use as well as safety issues. Because of the high temperatures, the transfer lines are to be extensively thermally insulated to allow manual handling when temperatures significantly higher than 90° C. are required. Also, in U.S. Pat. No. 6,487,920, the line end of the silcosteel tube is at ground potential. This is undesirable as it could result in electrocution, especially in a harsh and humid environment.

There is a need for an alternative form of transfer line which overcomes at least one of the disadvantages of the know transfer lines.

SUMMARY OF THE INVENTION

It is an object of the present invention to provide methods of sampling substances such as subsurface contaminants, and to provide a transfer line for use in a system for the sampling of substances such as subsurface contaminants as well as a sampling system and methods of manufacture and use of the system which is safer, lower in energy consumption and more efficient compared to the existing state of the art.

An aspect of the invention provides a transfer line for use in a probe system for subsurface chemical sampling, the transfer line for connecting an detection apparatus with a probe, the transfer line comprising:

a first flexible tube for carrying fluid to the probe; and a second flexible tube for carrying sample-loaded fluid from the probe;

wherein the second flexible or both first and second flexible tubes comprise a barrier tube surrounded by a metal coating and the metal coating of the second flexible or of both the first and second flexible tubes is surrounded by an insulating layer.

Preferably the barrier tube comprises at least on an inner surface thereof fused silica, PEEK or PTFE material.

The metal coating is preferably applied by a method such as plating to allow a thin layer to be deposited with structural integrity, i.e. a continuous cladding as an improvement over a discontinuous layer such as wrapped tapes.

The metal coating can be a nickel layer, an iron alloy, or a chrome alloy.

Optionally, both of the first and second flexible tubes can further comprise an insulation layer surrounding the metal coating.

For example the insulation layer can be a polyimide layer.

In an embodiment the second flexible tube or both the first and second flexible tubes further comprise a polymer layer positioned between the barrier tube and the metal coating.

For example, the polymer layer positioned between the barrier tube and the metal coating comprises a polyimide.

The inner diameter of the second flexible tube or both of the first and second flexible tubes an be less than substantially 0.7 mm and advantageously in the range 0.2-0.7 mm.

For example, the inner diameter of the second flexible tube or both of the first and second flexible tubes is/are in the range 0.2-0.7 mm.

Insulation sleeving can be provided to surround the second flexible tube or both the first and second flexible tubes. Flexible layers can be provided to surround the insulation sleeving and electrical wires can be provided for electrically connecting the surface apparatus to the probe which are positioned within the flexible layers or sleeving.

Preferably the metal coating is adapted to allow the second flexible tube or both the first and second flexible tubes to be heated in the temperature range from 30-350° C. by applying a voltage less than 200 or preferably less than 150 V to the metal coating.

The present invention also provides a probe system for subsurface chemical sampling comprising:
  a probe;
  a fluid source;
  a detector;
  a transfer line according to any one of the preceding claims, wherein the first flexible tube connects the fluid source to the probe and the second flexible tube connects the probe to the detector; and
  an electrical supply for applying a voltage to the metal coating of the second flexible tube or of both the first and second flexible tubes for heating the tube.

For example, one metal coating of the first or flexible tube is adapted as a heater while the metal coating of the other of the first and second flexible tubes is adapted to act as a temperature sensor.

In one embodiment the metal coatings of the first and second flexible tubes are electrically connected together.

The detector can be any suitable detector but for some applications it is preferred if the detector is adapted to detect VOC and SVOC compounds.

Embodiments of the present invention improve the transport of contaminants from the probe to a detector. The detector may be any suitable detector but is preferably a detector for VOC and SVOC compounds. An example is a gas chromatographic detector. The gas chromatographic detector may including any of: Dry Electrolytic Conductivity Detector—DELCD, Catalytic Combustion Detector—CCD, Thermal Conductivity Detector—TCD, Flame Ionization Detector—FID, Helium Ionization Detector—HID, Photo Ionization Detector—PID, Nitrogen-Phosphorus Detector—NPD, Thermionic Ionization Detector—TID, Flame Photometric Detector—FPD, Dual Flame Photometric Detector—Dual FPD, Electron Capture Detector—ECD, Halogen Specific Detector—XSD, Mass spectrometry—MS, etc. or combinations of these. Several detectors can be run in series for multiple chromatograms from one injection.

The present invention also provides a method of operating a probe system for subsurface chemical sampling, the probe system comprising a probe and a transfer line comprising a first flexible tube for carrying fluid to the probe, a second flexible tube for carrying sample-loaded fluid from the probe and wherein the second flexible or both tubes comprise a barrier tube surrounded by a metal coating, the method comprising:
  advancing the probe through a subsurface region;
  passing a carrier fluid through the first flexible tube of the transfer line to the probe;
  receiving sample-loaded fluid via the second flexible tube of the transfer line from the probe; and
  applying a voltage to the metal coating of the second flexible tube or of both the first and second flexible tubes to heat the tubes.

An advantage of embodiments of the present invention is to avoid certain disadvantages of the prior art heated transfer lines with which the tubes are heated by using a heating wire or tape wrapped around the tubes, which results in an inefficient and unequal heat transfer to the tubes, or are heated by using the tube itself as heating medium as in U.S. Pat. No. 6,487,920. Embodiments of the present invention can reduce the cross-contamination between samples which occurs when passing contaminant pure product zones (e.g. DNAPL's, Dense Non-Aqueous Phase layers, e.g. including tar and chlorinated solvents). When passing DNAPL's in accordance with embodiments of the present invention, compounds are not or less adsorbed on the inner wall of the transfer line. Therefore, the transfer line can be flushed with carrier gas in order to clean the transfer line. Flushing times can be reduced which is economically efficient.

Two temperature regimes can be identified. The first temperature regime is high enough to prevent condensation on the tube walls and is low enough to prevent temperature decomposition of the contaminants which are to be measured. Typically, for VOCs and SVOCs, this temperature lies in the range 120°-220° C. For low volatile compounds, the upper range can go to 350° C. The second temperature regime should be high enough to "bake out" the transfer line efficiently between two sampling events as to avoid cross contamination between samples and measurement in different time periods. This requires temperatures well above 200° C.

The flexible carrier tube and flexible collection tube according to embodiments of the invention can be heated, if required, to temperatures up to 350° C., thereby ensuring minimal adsorption/absorption within carrier tube. Moreover, also this heating can be achieved using very low electrical power, allowing efficient and safe handling when operated in the field.

BRIEF DESCRIPTION OF THE DRAWINGS

Embodiments of the invention will be described, by way of example only, with reference to the accompanying drawings in which.

DESCRIPTION OF PREFERRED EMBODIMENTS

Figure 1:
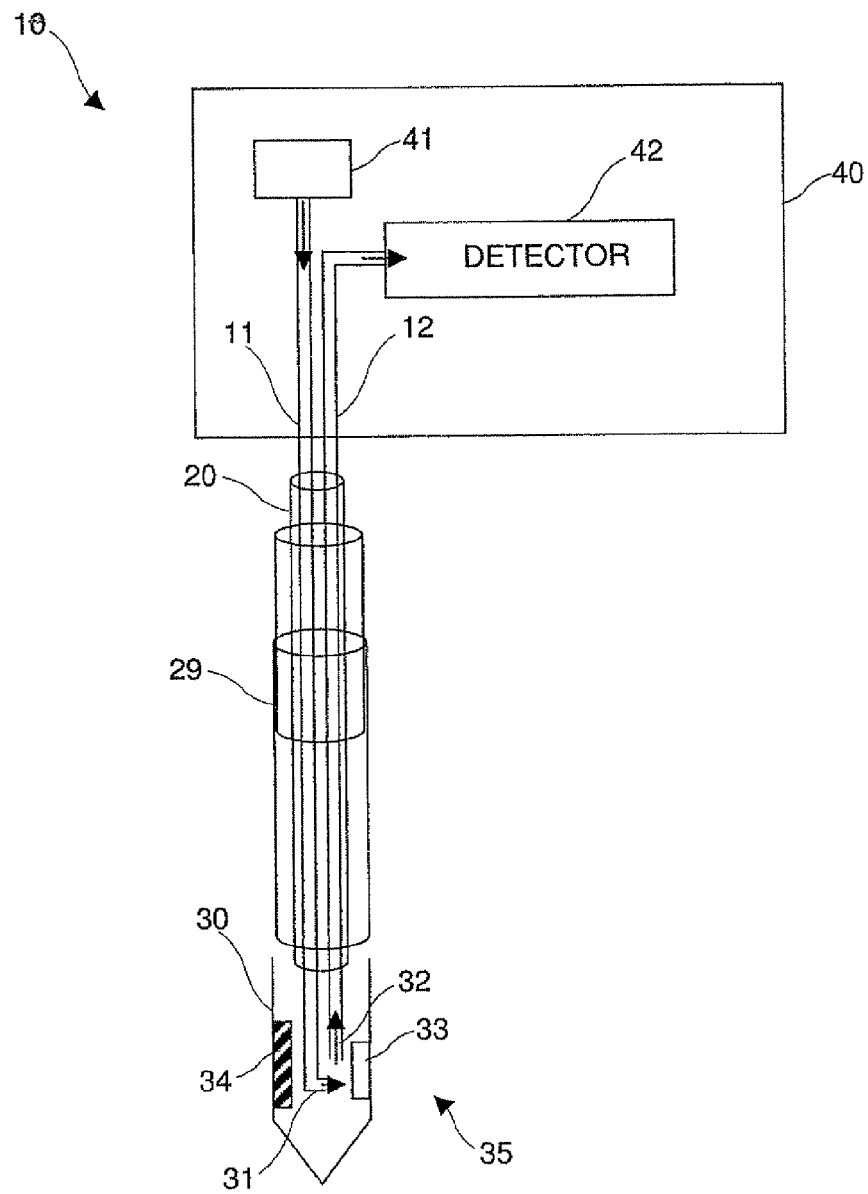
FIG. 1 shows a probe system for subsurface sampling.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Figure 2:
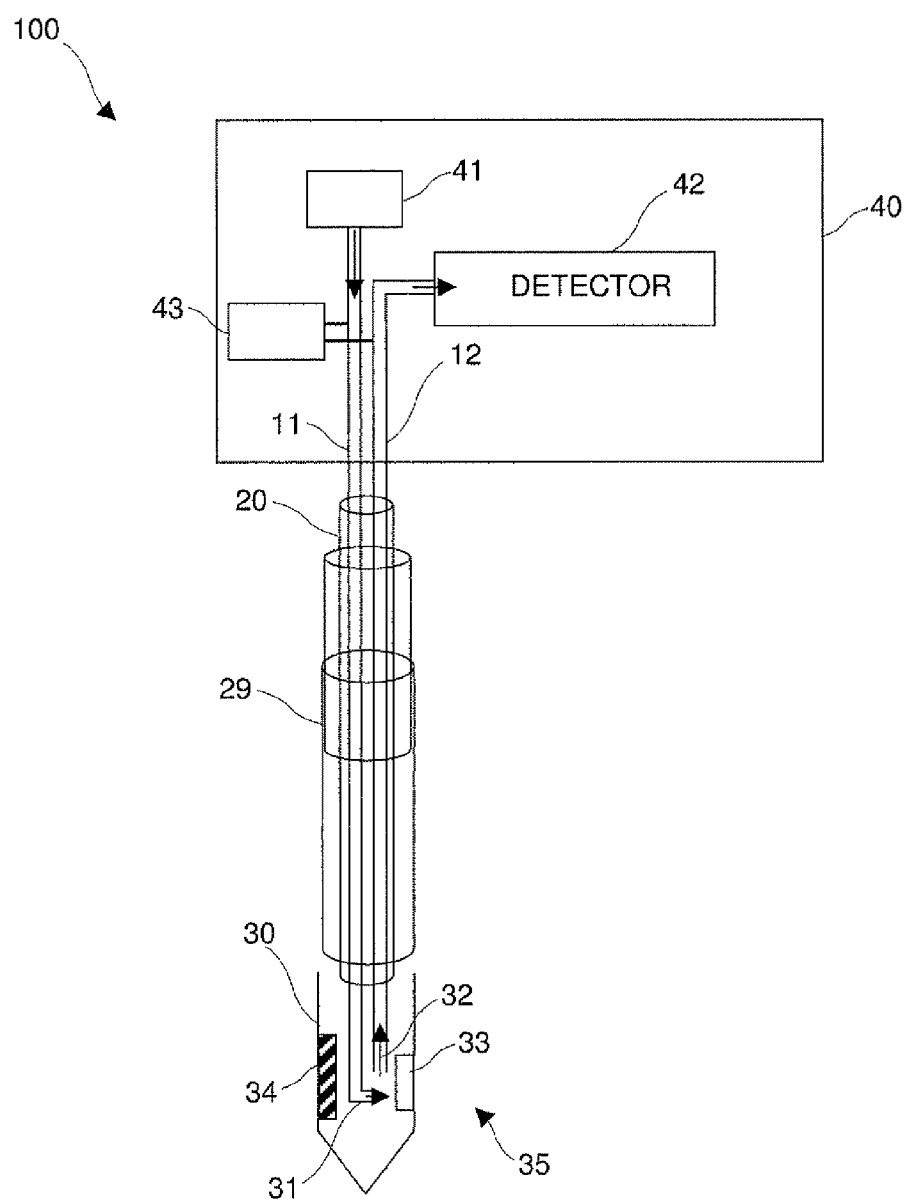
FIG. 2 shows a probe system for subsurface sampling according to an embodiment of the present invention.

FIG. 2 shows a probe system 100 for subsurface sampling according to an embodiment of the invention. The probe system 100 comprises a probe 30 which, in use in one embodiment, is advanced through soil by a pushing device such as a hydraulic pushing device (not shown). A set of pipes 29 connect the pushing device to the probe 30. A transfer line 20 is located in the interior of pipes 29. The transfer line 20 connects apparatus 40 on the surface with the probe 30. Apparatus 40 comprises a fluid source 41 connected to carrier tube 11 of the transfer line 20. The transfer line 20 is connected to any suitable equipment at the ground surface. For example a detector 42 can be connected to collection tube 12 of the transfer line 20. In use, fluid source 41 typically applies a carrier fluid such as a carrier gas under pressure to the carrier tube 11. However, the present invention is not restricted to injection of a carrier gas but also includes any other means of passing carrier gas through carrier tube 11 such as drawing the carrier gas through the carrier tube 11 by applying a vacuum at one end. The transfer line 20 typically comprises a carrier tube 11 for carrying gas in the direction from the surface apparatus 40 to the probe 30, a collection tube 12 for carrying gas in the direction from the probe 30 to the surface apparatus 40. In use, gas is delivered from the surface apparatus 40 to the probe 30 via tube 11. Contaminants in the heated soil in the region 35 around the probe 30 are collected in a collector, either directly, e.g. through an opening in the probe which allows hot gas to exit and contaminants to return or through a semi-permeable membrane. Contaminant-loaded gas is then conveyed, via tube 12, to the ground surface, e.g. to a detector 42 at the surface. The detector may be any suitable detector but is preferably a gas chromatographic detector for VOC and SVOC compounds. The detector may be a gas chromatographic detector, for example one of Dry Electrolytic Conductivity Detector—DELCD, Catalytic Combustion Detector—CCD, Thermal Conductivity Detector—TCD, Flame Ionization Detector—FID, Helium Ionization Detector—HID, Photo Ionization Detector—PID, Nitrogen-Phosphorus Detector—NPD, Thermionic Ionization Detector—TID, Flame Photometric Detector—FPD, Dual Flame Photometric Detector—Dual FPD, Electron Capture Detector—ECD, Halogen Specific Detector—XSD, Mass spectrometry—MS, etc. or combinations of these. Several detectors can be run in series for multiple chromatograms from one injection. An electrical supply 43 is provided for applying electrical power, e.g. to apply a voltage to the tubes 11, 12 for the purpose of heating the tubes 11, 12.

The transfer line 20 is required to be flexible as the line 20 must pass through the pipe sections 29 when they are stacked. Advantageously, the line should have a bending radius of approximately 30 cm or less. Also, as the internal diameter of the pipes 29 can be 20 mm (0.8"), there is a restriction for the outer diameter of the transfer line 20.

Figure 3:
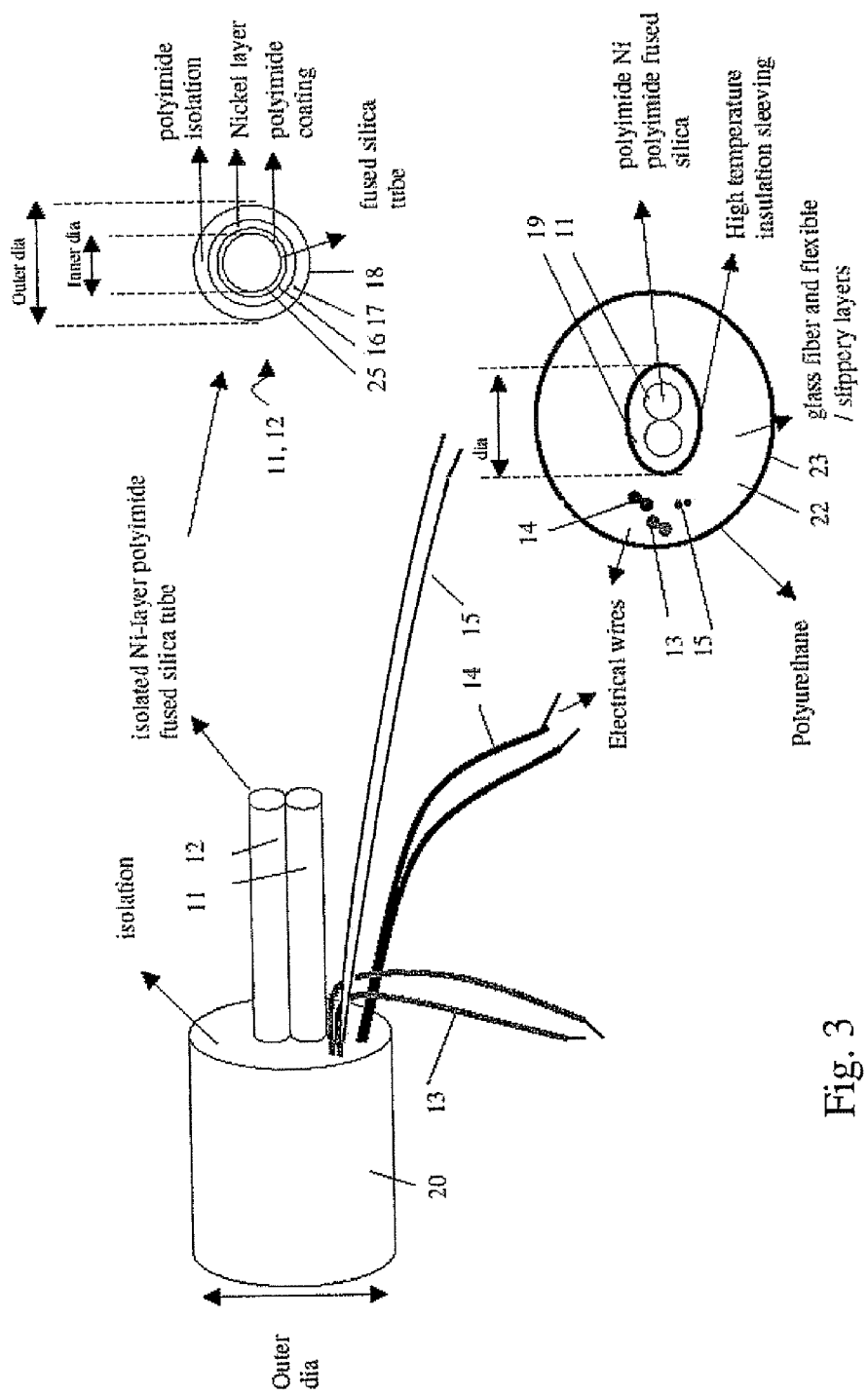
FIG. 3 shows a transfer line according to an embodiment of the present invention.

FIG. 3 shows an embodiment of the transfer line 20 in more detail. In addition to the tubes 11, 12, the transfer line comprises electrical wires 13, 14, 15. Wires 15 are for carrying an electrical supply to heat the probe 30, wires 13 are for conveying a signal from a thermocouple at the probe 30 to apparatus 40 and wires 14 are for conveying a signal from a conductivity sensor at the probe 30 to apparatus 40.

Each tube 11, 12 comprises a barrier tube. The barrier tube can be for example a deactivated fused silica lined tube 25. The barrier tube can also for example comprise a tube made of or lined with PTFE, PEEK or similar material. Optionally the barrier tube is provided with a temperature resisting polymer layer like PI, PEEK, PES, PU or mixtures of these materials. This layer may be a coating. In a preferred embodiment the polymer layer/coating is a polyimide layer/coating 16. The barrier tube such as the deactivated fused silica tube 25 prevents contaminants from being adsorbed or absorbed during their passage between the probe 30 and detector 42. The barrier tube 15 is also surrounded by a thin cladding or coating layer 17 of a metal. For example, the polyimide layer/coating 16 or the barrier tube 25 is coated with a thin layer 17 of a metal such as nickel, which can be heated resistively. The thin layer 17 of metal can be a plated layer. The polymer layer such as a polyimide coating hereby delivers extra physical strength to the barrier tube and provides a better adhesion/coating strength for the metal layer. Also other metals can be used other than nickel or in combination with nickel such as a nickel/chromium alloy, an iron/chrome/aluminium alloy. Such metals can be applied by a plating method. As the metal layer is to be heated resistively, and has to result in a uniform heating, the barrier tube should be surrounded around its circumference with the metal coating. Advantageously, the thickness of the nickel layer is 10-300 µm, preferably 50 µm. The thickness of the metal layer depends on and is limited by the resistivity of the metal used. High thicknesses of higher conductive metals are to be avoided, since these result in inefficient heating and increased stiffness.

Figures 4, 5:
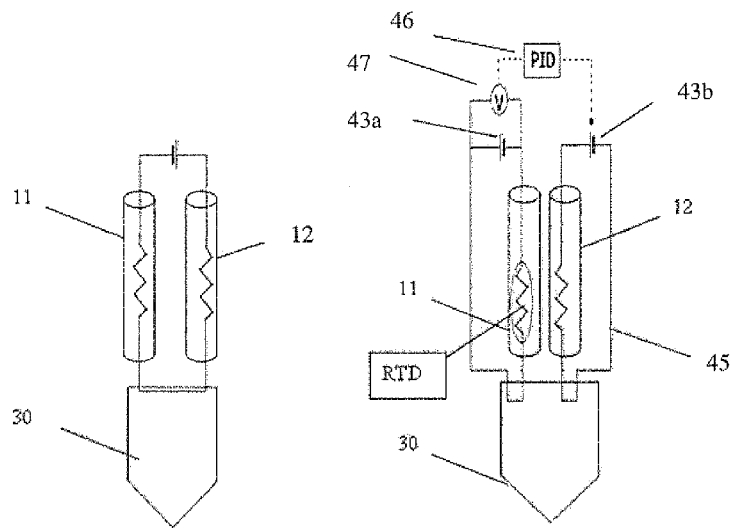
FIG. 4 shows a transfer line according to an embodiment of the present invention and its power source.
FIG. 5 shows a transfer line according to another embodiment of the present invention.

In use, the metal coating or cladding, e.g. nickel layer is resistively heated by the power source such as the voltage source 43, which can be voltage, current or power regulated (see FIGS. 1 and 4). The metal coated insulated barrier tube such as the nickel coated polyimide fused silica tube provides superior and uniform heat transfer to the lining of the barrier tube, e.g. the fused silica lining, preventing any cold areas in the tubes 11, 12. Since prior art heated transfer lines heat the tubes by wrapping a heating wire around the tubes or by use of a massive conductive tubing for resistive heating, the result is inefficient and unequal heat transfer to the tubes, requiring large power electrical power sources. Temperatures in the range of 120° C.-350° C. are needed to avoid condensation and/or to allow the debinding of chemicals from the barrier tube wall if adsorbed, to prevent cross-contamination between samples ("bake out"). The flexible heated carrier gas tube 11 and flexible heated collection gas tube 12 according to embodiments of the invention can be heated up to 350° C.

Figure 6:
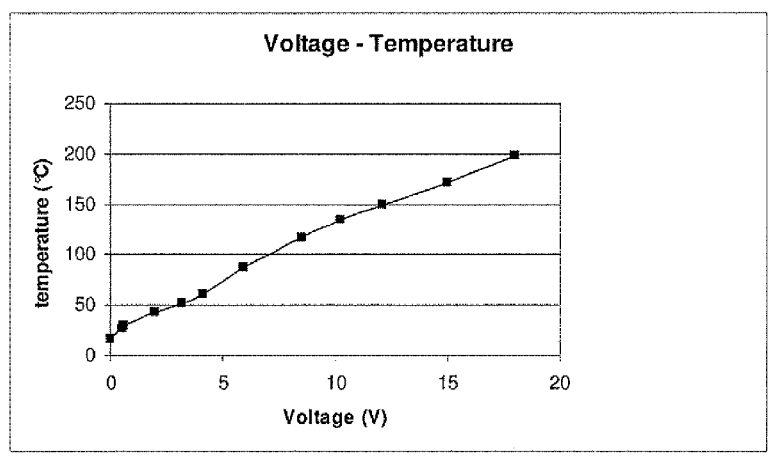
FIG. 6 shows the temperature reached as a function of the applied power for a 10 m polyimide and nickel layer fused silica tube, showing that only 80 W is necessary to achieve a temperature of 200° C.

A clear advantage of embodiments of the present invention is that the required temperatures can be acquired with low electrical power. FIG. 6 shows the temperature reached as a function of the applied power for a 10 m polyimide and nickel coated fused silica tube, showing that only 80 W is necessary to achieve a temperature of 200° C. Commercial systems available require powers up to 2-3 kW for heating the transfer line.

An outer insulating coating such as an outer polyimide coating 18 surrounds the metal, e.g. nickel layer 17. Coating 18 ensures at least the electrical insulation of the tube, the protection against mechanical wear of the metal layer and can also provide thermal insulation, reducing heat loss from the tube. As this outer coating, e.g. polyimide coating 18 is preferably very thin, the overall mass of the heated part of the tube is small. Keeping the mass of the heated part of the tube small minimises the power needed to heat the carrier and collection gas. Other thermoplastic or thermoharding polymers can be used as insulating coating. Given that only low voltages are applied, the coating can be very thin without the risk of electrical break down of the coating and short circuit. This insulating layer is crucial in guaranteeing the performance of the transport tube under all conditions under which is it used (winding, unwinding, storage in truck, guiding the tube up and down, . . . ) to prevent the tubes of from touching each other and creating shortcuts or other damage.

A high temperature resistant sleeving 19 preferably surrounds both tubes 11, 12 and further prevents the dissipated heat from escaping to the pipe sections and to the soil environment.

The inner diameter of the barrier tube, e.g. silica tube 11, 12 can be as small as 0.005 mm but is preferably in the range of 0.2-0.7 mm. Decreasing the diameter of the collection line results in less dilution of the sampled contaminants. As the gas flow for the membrane interface probe 30 is preferably 40 ml/min the gas speed in smaller tubes will be higher, resulting in less absorption of contaminants at the inner wall of the collection line. Increasing the gas speed will also result in a shorter response time of the detectors due to a faster transport of contaminants from the probe to the surface.

The metal layer such as the nickel layer 17 can be used as a heating element as shown in FIG. 4 in which the metal layers of tubes 11 and 12 are joined together in the probe 30 and a power source 43 is connected at ground level to the two metal layers. The metal layer such as the nickel layer 17 can also be used as the sensing element of a resistance temperature sensor for controlling the temperature of the collection tube, for example as shown in FIG. 5. The high sensitivity of the nickel layer 17 for temperature changes makes this an optimal choice for temperature control. In this embodiment the nickel layer of the collection gas tube acts as a resistive heater. In contrast, the nickel layer surrounding the carrier gas tube is used as a resistance temperature sensor (RTD). As shown in FIG. 5, in this assembly, additional electrical connections 45 are needed in order to connect the collection tube and the carrier gas tube to the voltage sources. Two power sources 43a and 43b are needed. The first controls the heating of the collection gas tube 12. The second, applies a small measurement current to the carrier gas tube—intermittently when measurements are taken for example. Due to the heat produced from the collection gas tube 12, the electrical resistance of the carrier gas tube 11 will change with temperature. Therefore, measuring the voltage using a voltmeter across the carrier gas tube 11, the power source 43b and so the heating of the collection gas tube 12 can be controlled by controller PID whereby a Proportional-Integral-Derivative controller is one kind of controller that can be used.

In an alternative embodiment the collection tube can act as temperature sensor while carrier gas tube acts as the heater.

Hence in some embodiments of the present invention the metal, e.g. nickel layer 17 of the collection tube works as heating device while the metal, e.g. nickel layer of the carrier gas tube works as a temperature sensor resistance element. Since, in this assembly, no thermocouples are used for temperature measurements along the transfer line, the overall diameter of the transfer line is significantly reduced. Secondly, since less components are embedded in the transfer line, there are less inter-layer movements of the transfer line when bending, improving the robustness of the transfer line.

However the present invention includes temperature control by using thermocouples which are located along the barrier tubes. Optionally thermocouples may be combined with using one of the metal, e.g. nickel layers as a temperature sensor.

Due to the decrease in mass of the heated part of the tube in comparison with other designs and due to the thin resistive metal coating, e.g. nickel layer 17, the voltage needed to heat the carrier gas tube 11 and collection gas tube 12 is 48 VDC, i.e. less than 200 or less than 150 volts, which is much less in comparison with other designs (240V).

Advantageously, the metal coatings, e.g. nickel layers 17 of the collection gas tube 12 and the carrier gas tube 11 are connected by an electrical wire in the probe (see FIG. 4). Therefore, the electrical connections are such that the electrical loop is closed. This is a major advantage in comparison with other designs where the probe is grounded. Closing the electrical loop creates a safer working space for the drilling team. Moreover, given only a low mass which needs to be heated, higher temperatures in the barrier tube can be reached which can be reached without needing to handle high temperature parts, and hence without the risk of physical injury. The metal coating, e.g. nickel layer of both tubes, i.e. the collection gas tube and carrier gas tube are connected by a electrical wire in the probe 30 which avoids the problem with connections of prior art designs here the probe is at ground level.

A method of acquiring a sample will now be described. Firstly, the probe 30 is located in a subsurface region where a sample is to be acquired. The probe is located by advancing the probe 30 from the surface, through a subsurface region (typically soil) to the required depth by applying a pressure such as a hydraulic pressure to a set of pipes 29. A transfer line 20 is located in the pipes 29, and connects the probe 30 to apparatus 40 at the surface. Fluid (typically a gas) is applied to tube 11 of the transfer line 20. The gas egresses the tube at port 31 within the probe. Contaminants, such as volatile organic compounds (VOC) and/or semi-volatile organic compounds (SVOC) pass through a membrane 33 of the probe and are swept by the gas flow into port 32 and along tube 12 to detector 42. Alternatively no semi-permeable membrane is used and instead an opening in the probe allows gas to exit and return loaded with contaminant. Detector 42 can perform, for example chemical analysis of the compounds within the gas. During the passage along tube 12, the gas flow is heated by the metal, e.g. nickel heating layer surrounding the tube 12. This prevents cooling of the gas flow and condensation within the tube 12. Electrical supply 43, 43a, 43b can supply voltage to the metal, e.g. nickel layer 17 of each tube 11, 12 to heat the tubes 11 and/or 12. In this way in one embodiments the gas can be heated as it passes along tube 11 towards the probe but this is not necessary for the invention. Optionally, the gas can be first or additionally heated at the probe by a probe heater 34. Heating both barrier tubes can have advantages because it reduces the overall power necessary and it provides for extra heating of the overall assembly, thus reducing power loss.

The invention is not limited to the embodiments described herein, which may be modified or varied without departing from the scope of the invention.

The invention claimed is:

1. A probe system for subsurface chemical sampling comprising:
a probe;
a fluid source;
a detector;
a transfer line comprising
a first flexible tube for carrying fluid to the probe; and
a second flexible tube for carrying sample-loaded fluid from the probe; wherein the first flexible tube connects the fluid source to the probe and the second flexible tube connects the probe to the detector; and an electrical supply for applying a voltage to the second flexible tube or to both the first and second flexible tubes for heating the second flexible tube, or both the first and second flexible tubes:

characterized in that the second flexible or both first and second flexible tubes comprise a barrier tube coated with a metal layer and the metal layer of the second flexible tube or of both the first and second flexible tubes is surrounded by an insulating layer, the voltage of the electrical supply being applied to said metal layer and the metal layer being arranged for providing a uniform heat transfer to the barrier tube; and wherein the second flexible tube or both the first and second flexible tubes further comprise(s) a polymer layer positioned between the barrier tube and the metal layer.

2. A probe system according to claim 1, wherein the barrier tube comprises at least on an inner surface thereof fused silica, PEEK or PTFE material.

3. A probe system according to claim 2, wherein the metal layer is a plated layer, or wherein the metal coating is a nickel layer, a nickel alloy, an iron alloy, or a chrome alloy.

4. A probe system according to claim 1, wherein the metal layer is a plated layer, or wherein the metal layer is a nickel layer, a nickel alloy, an iron alloy, or a chrome alloy.

5. A probe system according to claim 1, wherein said insulation layer comprises a polyimide layer.

6. A probe system according to claim 1, wherein the polymer layer positioned between the barrier tube and the metal layer comprises a polyimide.

7. A probe system according to claim 6, wherein the inner diameter of the second flexible tube or both of the first and second flexible tubes is/are in the range 0.2-0.7 mm.

8. A probe system according to claim 1, further comprising insulation sleeving surrounding the second flexible tube or both the first and second flexible tubes.

9. A probe system according to claim 8, wherein the metal coating layer is adapted to allow the second flexible tube or both the first and second flexible tubes to be heated in the temperature range from 30-350° C. by applying a voltage less than 200 to the metal layer.

10. A probe system according to claim 9, further comprising flexible layers surrounding the insulation sleeving and further comprising electrical wires for electrically connecting a surface apparatus to the probe which are positioned within the flexible layers.

11. A probe system according to claim 10, further comprising an outer sleeve surrounding the flexible tubes.

12. A probe system according to claim 11, wherein one metal coating of the first or second flexible tube is adapted as a heater while the metal coating of the other of the first and second flexible tubes is adapted to act as a temperature sensor, or wherein the metal coatings of the first and second flexible tubes are electrically connected together.

13. A probe system according to claim 9, wherein the temperature range is from 120° C. to 350° C.

14. A probe system according to claim 13, wherein the temperature achieved is 200° C. at an applied power of 80 watts.

15. A probe system according to claim 1, wherein one metal coating of the first or second flexible tube is adapted as a heater while the metal coating of the other of the first and second flexible tubes is adapted to act as a temperature sensor, or wherein the metal coatings of the first and second flexible tubes are electrically connected together.

16. A probe system according claim 15, wherein the detector is adapted to detect VOC and SVOC compounds, or wherein the detector is a gas chromatographic detector optionally selected from Dry Electrolytic Conductivity Detector—DELCD, Catalytic Combustion Detector—CCD, Thermal Conductivity Detector—TCD, Flame Ionization Detector—FID, Helium Ionization Detector—HID, Photo Ionization Detector—PID, Nitrogen-Phosphorus Detector—NPD, Thermionic Ionization Detector—TID, Flame Photometric Detector—FPD, Dual Flame Photometric Detector—Dual FPD, Electron Capture Detector—ECD, Halogen Specific Detector—XSD, Mass spectrometry—MS, or combinations of these.

17. A probe system according claim 1, wherein the detector is adapted to detect VOC and SVOC compounds, or wherein the detector is a gas chromatographic detector optionally selected from Dry Electrolytic Conductivity Detector—DELCD, Catalytic Combustion Detector—CCD, Thermal Conductivity Detector—TCD, Flame Ionization Detector—FID, Helium Ionization Detector—HID, Photo Ionization Detector—PID, Nitrogen-Phosphorus Detector—NPD, Thermionic Ionization Detector—TID, Flame Photometric Detector—FPD, Dual Flame Photometric Detector—Dual FPD, Electron Capture Detector—ECD, Halogen Specific Detector—XSD, Mass spectrometry—MS, or combinations of these.

18. A probe system of claim 1, wherein both the first and second flexible tube comprise a fused silica barrier tube with an inner diameter of from 0.2-0.7 mm and the metal layer is a nickel layer which has a thickness of 10-300 μm.

19. A probe system of claim 18, wherein the thickness of the nickel layer is 50 μm.

20. A probe system according to claim 18, wherein the second flexible tube or both the first and second flexible tubes further comprise(s) a polymer layer positioned between the barrier tube and the metal layer.

21. A probe system according to claim 20, wherein said polymer layer comprises a polyimide layer.

22. A probe system according to claim 21, wherein said insulation layer comprises a polyimide layer.

23. A probe system for subsurface chemical sampling comprising:
    a probe;
    a fluid source;
    a detector;
    a transfer line comprising
a first flexible tube for carrying fluid to the probe; and
a second flexible tube for carrying sample-loaded fluid from the probe; wherein the first flexible tube connects the fluid source to the probe and the second flexible tube connects the probe to the detector; and
    an electrical supply for applying a voltage to the second flexible tube or to both the first and second flexible tubes for heating the tube, characterized in that the second flexible tube or both first and second flexible tubes comprise a barrier tube, a metal coating layer, an insulating layer,
the metal coating layer, of the second flexible tube or both the first and second flexible tubes, surrounding the barrier tube;
the insulating layer surrounding the metal coating;
the electrical supply being arranged for applying a voltage to the metal coating for heating it resistively;
the barrier tube being arranged for transferring the heat of the metal coating to the fluid carried by the barrier tube.

* * * * *